(12) United States Patent
Pleydon et al.

(10) Patent No.: US 11,959,056 B2
(45) Date of Patent: Apr. 16, 2024

(54) CELL CULTURE SYSTEM

(71) Applicant: Saint-Gobain Performance Plastics Corporation, Solon, OH (US)

(72) Inventors: Robert G. Pleydon, Worcester, MA (US); Natasha Anna Boghosian, Boston, MA (US); Jacob Andrews, Washington, DC (US); Phillippe Jean Broussard, Finksburg, MD (US)

(73) Assignee: Saint-Gobain Performance Plastics Corporation, Solon, OH (US)

( * ) Notice: Subject to any disclaimer, the term of this patent is extended or adjusted under 35 U.S.C. 154(b) by 835 days.

(21) Appl. No.: 16/917,331

(22) Filed: Jun. 30, 2020

(65) Prior Publication Data
US 2020/0407670 A1    Dec. 31, 2020

Related U.S. Application Data

(60) Provisional application No. 62/869,021, filed on Jun. 30, 2019.

(51) Int. Cl.
| C12M 1/00 | (2006.01) |
| C12N 1/04 | (2006.01) |
| C12N 5/0786 | (2010.01) |

(52) U.S. Cl.
CPC ............ *C12M 23/14* (2013.01); *C12M 29/00* (2013.01); *C12N 1/04* (2013.01); *C12N 5/0645* (2013.01)

(58) Field of Classification Search
None
See application file for complete search history.

(56) References Cited

U.S. PATENT DOCUMENTS

| 4,537,860 A | 8/1985 | Tolbert |
| 5,057,429 A * | 10/1991 | Watanabe ............... C12M 25/02 |
| | | 435/297.1 |

(Continued)

FOREIGN PATENT DOCUMENTS

| CN | 103361271 A | 10/2013 |
| CN | 105925481 A | 9/2016 |

(Continued)

OTHER PUBLICATIONS

International Search Report and Written Opinion in PCT/US2020/040330, dated Oct. 21, 2020.

*Primary Examiner* — Holly Kipouros
(74) *Attorney, Agent, or Firm* — McDonnell Boehnen Hulbert & Berghoff LLP (57) ABSTRACT

The disclosure relates generally to a cell culture apparatus and a cell culture method. One aspect of the disclosure provides a perfusion cell culture bag comprising one or more polymer films, having edges bonded together to form edges around an undivided interior compartment of the bag; first and second ports each formed in an exterior surface of the bag; first and second liquid-permeable tubes each extending into and in fluid communication with the interior compartment of the bag and operatively coupled to a respective port; and a third port formed in an exterior surface of the bag, the third port being in fluid communication with the interior compartment of the bag; wherein the first tube comprises a first inner support structure defining a central lumen of the tube and a first outer filter layer surrounding the first inner support structure.

20 Claims, 3 Drawing Sheets

(56) References Cited

U.S. PATENT DOCUMENTS

| | | |
|---|---|---|
| 5,079,168 A | 1/1992 | Amiot |
| 2003/0036192 A1* | 2/2003 | Singh ................... B01F 31/23 |
| | | 435/297.2 |
| 2012/0238011 A1 | 9/2012 | Tuohey |
| 2014/0011270 A1 | 1/2014 | Chotteau |
| 2014/0287512 A1* | 9/2014 | Kaisermayer .......... C12M 27/16 |
| | | 435/456 |
| 2016/0177245 A1 | 6/2016 | Johnson |
| 2016/0177246 A1 | 6/2016 | Lundgren |
| 2017/0197055 A1 | 11/2017 | Moody |
| 2018/0127797 A1 | 5/2018 | Brutinel |
| 2018/0346864 A1 | 12/2018 | Faldt |
| 2019/0001273 A1 | 1/2019 | Zhou |
| 2019/0017009 A1 | 1/2019 | Yu |
| 2020/0360838 A1* | 11/2020 | Goral .................... B01D 15/22 |
| 2020/0399572 A1* | 12/2020 | Kim ...................... C12M 23/14 |
| 2021/0054327 A1* | 2/2021 | Pearsons ............... C12M 23/14 |
| 2021/0071123 A1* | 3/2021 | Saukkonen ............ C12M 23/14 |

FOREIGN PATENT DOCUMENTS

| | | |
|---|---|---|
| JP | 2010136628 A | 6/2010 |
| WO | 2015148916 A2 | 10/2015 |
| WO | 2017189218 A2 | 11/2017 |

\* cited by examiner

CELL CULTURE SYSTEM

CROSS-REFERENCE TO RELATED APPLICATIONS

This application claims the benefit of priority of U.S. Provisional Patent Application No. 62/869,021, filed Jun. 30, 2019, which is hereby incorporated herein by reference in its entirety.

BACKGROUND OF THE DISCLOSURE

Field of the Disclosure

The disclosure relates generally to a cell culture apparatus and a cell culture method.

Technical Background

In vitro cell culture is the complex process by which cells are grown under controlled conditions, generally outside of a natural environment but as close to in vivo conditions as possible. In practice, cell culture refers to the culturing of cells derived from multi-cellular eukaryotes, especially animal cells. However, plants, fungi, insects and microbes including viruses, bacteria and protista can also be cultured.

In vitro cell culture can provide material for research and application in pharmacology, physiology, and toxicology. Cell cultures are also necessary aspects of bioprocessing and cell therapy.

Cells can be grown and maintained at an appropriate temperature and gas mixture in a cell incubator. Typically, mammalian cells are incubated at 37° C. with a pH maintained between 7.2 and 7.4. The pH can be controlled using a bicarbonate buffering system in the medium in conjunction with an incubator atmosphere of approximately 5-7 vol. % carbon dioxide. Carbon dioxide reacts with water to form carbonic acid, which in turn interacts with bicarbonate ions in the medium to form a buffering system that can maintain the pH near physiological levels. Oxygen is essential for cellular metabolism and growth for many desirable cell types. Culture conditions can vary for each cell type, and variation of conditions for a particular cell type can result in the expression of different phenotypes. For instance, bicarbonate-based buffers can be substituted with mono- and di- or tri-sodium phosphate buffers, chloride and ammonia buffers, lactate, or organic buffers such as HEPES, etc.

Monocytes are the largest type of white blood cells (leukocytes) and are an important part of the innate immune system of vertebrates including all mammals. Monocytes are the circulating precursors of macrophages and dendritic cells that migrate from the blood stream across vascular endothelium for immunological surveillance and inflammation response. Monocytes are often grown in cell culture.

T-Cells play an important role in immune response. They develop in the thymus gland, and are present in various populations in humans. Adoptive T-cell therapy is a rapidly progressing field, and so methods for growing T-cells in culture are desirable.

Commercially available cell culture devices in the form of bags are a conventional format used for cell culture. Cell culture bags have the advantage of being disposable, which reduces preparation and clean up time. Additionally, cell culture bags are pre-sterilizable, inexpensive, easy to use and require minimal space for storage and use. Disposables also help reduce the risk of contamination for the cell culture and for the environment.

However, one problem of conventional fluoropolymer cell culture bags is that the feed media and cells are mixed within the culture chamber and therefore the amount of media added is limited to the volume of the container. Another problem of conventional fluoropolymer cell culture bags is removal of media having diminished nutrient content (e.g., glucose) and increased waste content (e.g., lactate) during cell cultivation, which may unavailingly remove cells as well. Additionally, manual manipulation of the culture is typically necessary to replenish the medium.

Perfusion is a continuous process in which an adherent or suspension cell culture in a bioreactor is continuously supplied with fresh medium while spent culture media is continuously removed. Cells are continuously filtered from the spent culture media and returned to the bioreactor to maintain a constant culture volume. This continuous process allows for sustainable cell densities as high as of 10-15 million cells/mL. However, this process is conventionally limited to complex perfusion bioreactors that require large volumes of media. Moreover, the filtration and return of cells from the spent culture media can undesirably disturb the cell culture.

Therefore, a need exists for a simplified perfusion apparatus that allows removal and replenishment of feed media without appreciably disturbing cells and/or diminishing cell count.

SUMMARY OF THE DISCLOSURE

One aspect of the disclosure is a bag comprising one or more polymer films (e.g., a first polymer film and a second polymer film), having edges bonded together to form edges around an undivided interior compartment of the bag; a first port formed in an exterior surface of the bag; a first liquid-permeable tube extending into and in fluid communication with the interior compartment of the bag, the first tube being operatively coupled to the first port; a second port formed in an exterior surface of the bag; a second liquid-permeable tube extending into and in fluid communication with the interior compartment of the bag, the second tube being operatively coupled to the second port; and, optionally, a third port formed in an exterior surface of the bag, the third port being in fluid communication with the interior compartment of the bag; wherein the first tube comprises a first inner support structure defining a central lumen of the tube and a first outer filter layer surrounding the first inner support structure.

Another aspect of the disclosure is a bag comprising one or more polymer films (e.g., a first polymer film and a second polymer film), having edges bonded together to form edges around an undivided interior compartment of the bag; a first port formed in an exterior surface of the bag; a first liquid-permeable tube extending into and in fluid communication with the interior compartment of the bag, the first tube being operatively coupled to the first port; a second port formed in an exterior surface of the bag; a second liquid-permeable tube extending into and in fluid communication with the interior compartment of the bag, the second tube being operatively coupled to the second port; and, optionally, a third port formed in an exterior surface of the bag, the third port being in fluid communication with the interior compartment of the bag; wherein the first tube has an average pore size of no more than 50 microns, for example, no more than 20 microns, or even no more than 10 microns.

Another aspect of the disclosure is a cell culture system comprising a bag (e.g., according to any embodiment as described herein) oriented on a support such that the first and second liquid-permeable tubes are elevated relative to a majority of the first polymer film of the bag.

Another aspect of the disclosure is a cell culture system comprising a bag (e.g., according to an embodiment as described herein) oriented on a support such that the first liquid-permeable tube is elevated relative to the second liquid-permeable tube.

Another aspect of the disclosure is a method for cultivating cells, comprising providing a bag (e.g., according to an embodiment as described herein) including media and cell in the interior compartment; and flowing media through the interior compartment by adding media through the second port and through the second liquid-permeable tube and removing media through the first liquid-permeable tube and through the first port.

DETAILED DESCRIPTION

The disclosure relates to bags having an interior compartment, the bag including a first port coupled to a first liquid-permeable tube extending into and in fluid communication with the interior compartment, a second port coupled to a second liquid-permeable tube extending into and in fluid communication with the interior compartment, and, optionally, a third port in fluid communication with the interior compartment. At least the first tube comprises a first inner support structure and a first outer filter layer surrounding the first inner support structure. The disclosure demonstrates that, advantageously, feed media can be perfused through the interior compartment of the bag without appreciably disturbing cells and/or diminishing cell count by flowing media from the second tube, through the interior volume, and out of the first tube. The first filter layer of the first tube can prevent cells from escaping the interior volume of the interior compartment. The disclosure further demonstrates that cells can thus be grown and concentrated in the interior compartment without feed media supply limitations and/or waste removal limitations. When present, the third port can be used for media sampling and cell introduction into and removal from the interior compartment.

Accordingly, one aspect of the disclosure is a bag comprising one or more polymer films (e.g., a first polymer film and second polymer film), having edges bonded together to form edges around an undivided interior compartment of the bag. The bag includes a first port formed in an exterior surface of the bag and a first liquid-permeable tube extending into and in fluid communication with the interior compartment of the bag, the first tube being operatively coupled to the first port. The bag includes a second port formed in an exterior surface of the bag and a second liquid-permeable tube extending into and in fluid communication with the interior compartment of the bag, the second tube being operatively coupled to the second port. The bag optionally includes a third port formed in an exterior surface of the bag, the third port being in fluid communication with the interior compartment of the bag. The first tube and the second tube both extend in the direction of a first axis (e.g., a major axis) of the interior compartment of the bag; and the first tube comprises a first inner support structure defining a central lumen of the tube and a first outer filter later surrounding the first inner support structure.

In certain embodiments, the one or more polymer films include a first polymer film and a second polymer film, having edges bonded together to form edges around an undivided interior compartment of the bag. However, in other embodiments, a single film can be folded over and bonded to itself to form the bag, or a tubular film can be welded on two edges to form the bag.

Notably, the interior compartment need not be divided. In certain desirable embodiments of the bags as otherwise described herein, there is no membrane or other porous structure that divides the interior compartment such that the first and second tubes are in a first sub-compartment and a third port is connected to a second sub-compartment divided from the first sub-compartment by the membrane or other porous structure. That is, in certain desirable embodiments, there is no membrane or other porous structure operatively disposed between the first and second fluid-permeable tubes and a third port (i.e., such that fluid would need to pass between such membrane or other porous structure to flow between the first or second fluid-permeable tube and the third port). This can advantageously allow for good fluid transfer between the incubating cells and the perfused media.

Figure 1:
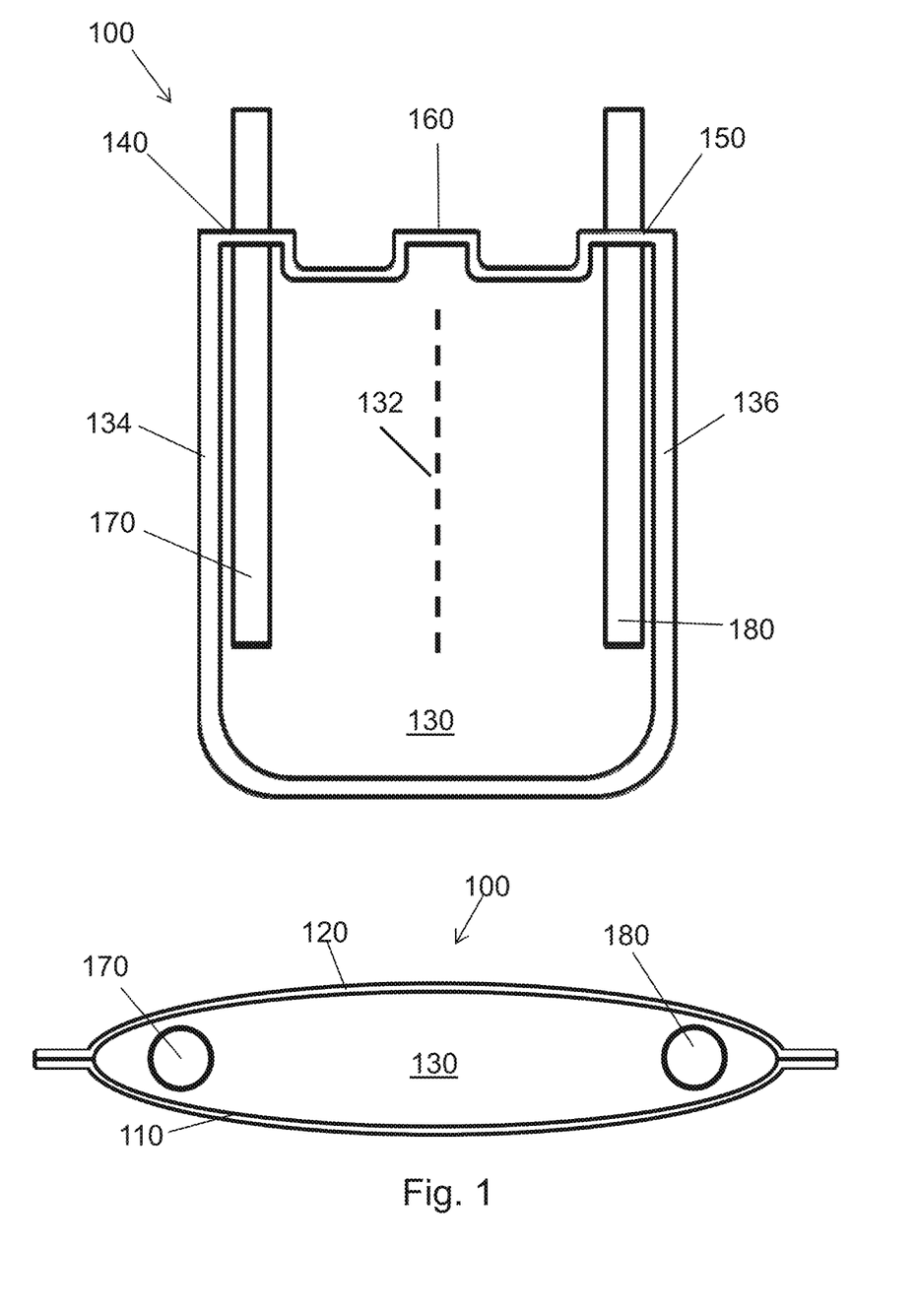
FIG. 1 is a schematic top-down (top) and cross-sectional (bottom) view of a bag according to one embodiment of the disclosure.

An embodiment of such a bag is shown in schematic top-down view (left) and cross-sectional view (right) in FIG. 1. Bag 100 of FIG. 1 includes a first polymer film 110 and a second polymer film 120, bonded together at edges thereof to form edges around an undivided interior compartment 130 having a major axis 132. Bag 100 further includes first port 140, operatively coupled to a first liquid-permeable tube 170, and second port 150, operatively coupled to a second liquid-permeable tube 180. In the embodiment of FIG. 1, Bag 100 further includes third port 160 in fluid communication with interior compartment 130; however, the person of ordinary skill in the art will appreciate that the third port need not be present in all embodiments contemplated herein.

In various embodiments as described herein, the thickness of first polymer film and second polymer film can vary upon application and desired container volume and permeability. The thickness of polymer films 110 and 120 may be, for example, in the range of 1 mil (i.e., 1 mil=0.001 inch, or 25.4 microns) to 30 mils. In certain embodiments, the thicknesses of the polymer films is in the range of 5 mils to 10 mils.

The bags described herein can be provided in a variety of volumes. Though not particularly limited, the volume of interior compartment can be, for example, in the range of 5 mL to 3500 mL, e.g., from 10 mL to 500 mL, or from 10 mL to 100 mL, or from 100 mL to 3000 mL, or from 500 mL to 2500 mL, or from 500 mL to 2000 mL. But as the person of ordinary skill in the art would appreciate, bags of different volumes are also contemplated.

The bag is desirably configured to allow perfusion of media through a substantial portion of the interior volume by flowing from the second liquid-permeable tube to the first liquid-permeable tube. In certain desirable embodiments, the first tube is disposed adjacent a first lateral edge of the bag, and the second tube is disposed adjacent a second, opposed, lateral edge of the bag; in certain embodiments, each is within 2 cm of a lateral edge of the bag. For example, in the embodiment of FIG. 1, the first tube 170 is disposed adjacent first lateral edge 134, and the second tube 180 is disposed adjacent second lateral edge 136, which is on an opposite side of the bag from the first lateral edge 134. The tubes can be, for example, substantially parallel to one another, e.g., within 20 degrees or even within 10 degrees of one another. In certain desirable embodiments, the first tube and the second tube extend along the direction of a major axis of the bag. For example, in the embodiment of FIG. 1, the first tube 170 and the second tube 180 extend along the direction of the major axis 132 of the bag. Of course, the tubes can in other embodiments be arranged in any suitable manner. For example, in certain embodiments, the first tube and second tubes are curved, and extend along the lateral edges of a rounded bag.

The first, second and (if present) third ports can be located at a variety of positions along the bag. For example, in certain embodiments, the first and second ports are formed at edges of the bag, e.g., edges extending orthogonally to the direction of the extension of the tubes into the bag. This can be in the same edge as shown in FIG. 1, or in opposing edges. This allows the relative positions of the first and second ports to facilitate extension of the first liquid-permeable tube and the second liquid-permeable tube along a common direction (e.g., along a major axis of the bag). The third port can be formed, for example, along the same edge as one or both of the first and second port; in the embodiment of FIG. 1, ports 140, 150, and 160 are along a common edge. But the third port can alternatively be along an edge that is orthogonal to the edge(s) in which the first and second ports or formed, or, alternatively along another surface of the bag, e.g., along a bottom surface to allow for gravity-assisted removal of cells. The positions of the ports are not particularly limited, provided the relative positions of the first and second ports (and the first and second tubes coupled thereto) facilitate perfusion through a substantial volume of the bag. The person of ordinary skill in the art will, based on the present disclosure, arrange the first tube and the second tube, e.g., to minimize dead spots in perfusion flow within the bag, and/or to ensure that perfusing flow does not disturb cell growth. When present, the third port can be positioned e.g., to facilitate introduction of cells to and/or collection of cells from the interior volume of the bag, or to provide for a desired position of fluid sampling or monitoring in the bag.

The one or more polymer films defining the interior compartment of the bag can have one or more desirable characteristics including, for example, gas permeability (and specifically oxygen permeability) or in other embodiments gas impermeability (and specifically oxygen impermeability), flexibility, heat-sealability that ensures watertightness, good clarity that permits the microscopic evaluation of cell growth, freedom from plasticizers (such as dioctyl phthalate and diisodecyl phthalate) that can be harmful to cells, moisture vapor transmission, capacity to be altered for desired cell interaction with cells, optical clarity, and physical strength. In certain desirable embodiments, one or more of the polymer films (e.g., each of the polymer films defining the interior compartment) are gas permeable and can allow diffusion of oxygen (necessary for cellular growth) and diffusion of carbon dioxide (waste product; necessary to buffer pH) into and out of the interior compartment. For example, in certain embodiments, one or more of the polymer film(s) defining the bag are oxygen-permeable multilayer films, such as the fluoropolymer/silicone films described in U.S. Pat. No. 9,926,524, which is hereby incorporated herein by reference in its entirety. In certain embodiments, one or more of the polymer film(s) defining the bag is a fluoropolymer film, such as fluorinated ethylene-propylene (FEP), polytetrafluoroethylene (PTFE), polyvinylidenefluoride (PVDF), tetrafluoroethylene-perfluoro (propyl vinyl ether) (PFA), polyvinylidene difluoride (PVF), polychlorotrifluoroethylene (PCTFE), tetrafluoroethylene/hexafluoropropylene/ethylene copolymer(HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers(TFE/P), tetrafluoroethylene/hexafluoropropylene copolymers (FEP/HFP), or hexafluoropropylene/tetrafluoroethylene/vinylidene copolymer (THV). In certain embodiments, one or more of the polymer films defining the bag is a film of fluorinated ethylene propylene copolymer (FEP). And in other embodiments, one or more of (e.g., each of) the polymer film(s) defining the bag is an oxygen-impermeable film. In such embodiments, the exchange of oxygen into and out of the bag can be managed using the perfused media.

The surfaces of one or more of the polymer films (e.g., one or more surfaces defining the interior compartment) can be treated, for example, by C-treatment, corona discharge, plasma treatment, etching, or combinations thereof. The surfaces can also be chemically treated, for example, with additives or primers (e.g., used alone or in conjunction with other treatment methods).

To form the bag, edges of the one or more polymer films can be bonded by any desirable method, such as RF welding, thermal impulse welding, ultrasonic welding, hot bar welding, chemical bonding, adhesive bonding, thermal fusion bonding, solvent welding, laser welding, corona discharge, radiation, surface treatment, extreme heat, belt, or melt lamination, etching, plasma treatment, extrusion, wetting, adhesives, or combinations thereof. In certain desirable embodiments, the one or more films are bonded by thermal, laser, or hot bar welding.

The first tube and the second tube can be attached to respective first and second ports formed in one or more edges of the bag by a collar sealing process (e.g., by RF welding, ultrasonic welding, thermal impulse welding, hot bar welding, chemical bonding, adhesive bonding, thermal fusion bonding, solvent welding, laser welding, corona discharge, radiation, extreme heat or melt lamination, etching, plasma treatment, wetting, adhesives, or combinations thereof). This can be done at the time of formation of the bag. The first tube can be sealed (e.g., by collar sealing) such that its outer filter layer can prevent cells from being transmitted from the interior compartment through the tube and out the first port. Thus, the first and/or second tubes can extend from outside the bag into inside the bag (with porous parts thereof desirably extending substantially only in the bag). Of course, in other embodiments, the first and/or second tubes can be terminated at the bag, and be connected through to a fluid system through other tubing; such other tubing can be made from the same materials as described herein for the first and second fluid-permeable tubes.

As noted above, in certain embodiments the first tube (e.g., tube 170 of FIG. 1) comprises a first inner support structure defining a central lumen of the tube and a first outer filter layer surrounding the first inner support structure. As described in detail herein, the first inner support structure can take a variety of forms, e.g., a perforated or otherwise porous tube, a frame, or a spiral-wound filament. The support structure can be round in cross-section as shown in the Figures herein, or can have other cross-sectional shapes, e.g., polygonal. In certain desirable embodiments as otherwise described herein, the materials of the support structure and outer filter layer are hydrophilic, self-wetting, and/or of sufficient porosity such that liquid flow through the tube can be initiated or maintained with minimal pressure.

Figure 2:
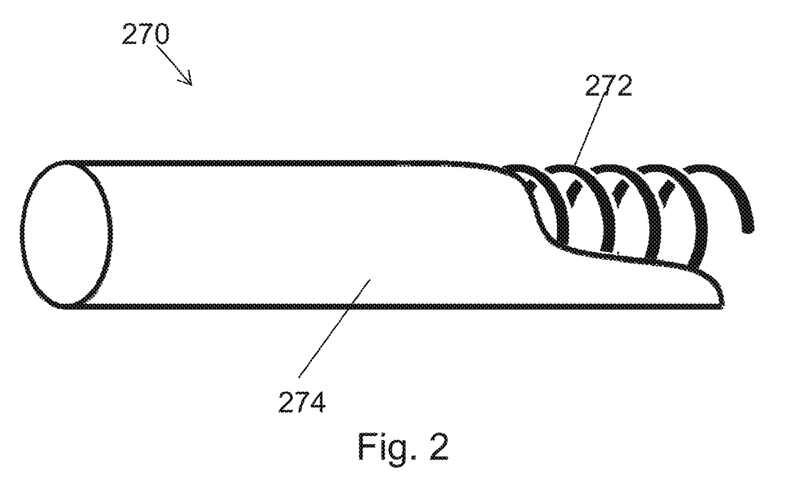
FIG. 2 is a schematic cutaway view of a liquid-permeable tube according to one embodiment of the disclosure.

An embodiment of such a fluid-permeable tube is shown in cutaway view in in FIG. 2. Tube 200 of FIG. 2 includes a spiral-wound filament 272 and an outer filter layer 274 surrounding the filament. Outer filter layer 274 is attached to spiral-wound filament 272 at least at the port (e.g., port 140 of FIG. 1) but can be attached to spiral-wound filament 272 at one or more additional points along the filament. The outer filter layer can relatively loosely surround the spiral-wound filament (e.g., as a loose bag over filament 272), or can be disposed more tightly against the spiral-wound filament (e.g., as a close-fitting sleeve over filament 272).

Accordingly, in certain embodiments as otherwise described herein, the first inner support structure comprises a spiral-wound filament. The filament can be relatively rigid or relatively flexible and can be wound relatively tightly or relatively loosely, provided, of course, that the filament defines a central lumen of the tube and can support the first outer filter layer. In certain desirable embodiments as otherwise described herein, the filament comprises (e.g., is) a polymer having a total organic carbon in water of less than 0.1 mg/cm$^2$. In certain embodiments as otherwise described herein, the filament comprises (e.g., is formed of) a fluoropolymer, polymethylpentene, or a combination thereof (e.g., having a total organic carbon in water of less than 0.1 mg/cm$^2$).

In certain embodiments as otherwise described herein, the spacing of the spiral-wound filament (i.e., along an axis of the central lumen) is about equivalent to or even larger than the size of most cells. For example, in certain embodiments as otherwise described herein, the spacing of the spiral-wound filament is at least 100 μm, or within the range of 100 μm to 10 mm, or 500 μm to 7.5 mm, or 1 mm to 5 mm. The present inventors have determined that a tube having a spacing of larger than 100 μm can advantageously facilitate culture media perfusion at a desirable flow rate, without appreciably disturbing and/or diminishing the count of cultured cells.

In other embodiments as otherwise described herein, a support structure can be provided as a frame, e.g., formed from filament-shaped material, but arranged differently than in a spiral. The filament and spacing of filaments can be as described above for the spiral-wound filament.

In other embodiments as otherwise provided herein, the support structure can be in the form of a porous tube. One such embodiment (e.g., for use as tube 170 of FIG. 1) is shown in cutaway in FIG. 3. Tube 370 of FIG. 3 includes a porous tube 372 and an outer filter layer 374 surrounding the porous tube. The outer filter layer is attached to the porous tube at least at the port (e.g., port 140 of FIG. 1) but can be attached to the porous tube at one or more additional points along the tube. The outer filter layer can relatively loosely surround the porous tube (e.g., as a bag over porous tube 372), or can be disposed more tightly against the porous tube (e.g., as a sleeve over porous tube 372).

Accordingly, in certain embodiments as otherwise descried herein, the first inner support structure comprises a first porous tube. The tube can be relatively flexible or relatively rigid, provided, of course, that the tube can support the first outer filter layer. In certain desirable embodiments as otherwise described herein, the porous tube comprises (e.g., is formed of) a polymer having a total organic carbon in water of less than 0.1 mg/cm$^2$. In certain embodiments as otherwise described herein, the porous tube comprises (e.g., is formed of) an elastomer, fluoropolymer, polymethylpentene, or a combination thereof (e.g., having a total organic carbon in water of less than 0.1 mg/cm$^2$). In certain desirable embodiments as otherwise described herein, the porous tube comprises (e.g., is formed of) silicone or polyvinyl chloride (e.g., having a total organic carbon in water of less than 0.1 mg/cm$^2$). For example, in certain such embodiments, the porous tube comprises a silicone elastomer. In another example, in certain such embodiments, the porous tube comprises fluorinated ethylene propylene. But a variety of fluorinated and non-fluorinated polymers can otherwise be used, as can other suitable materials.

In certain embodiments as otherwise described herein, the porous tube has an average pore size within the range of 1 μm to 5,000 μm. For example, in certain embodiments as otherwise described herein, the average pore size of the porous tube is within the range of 1 μm to 2,000 μm, or 1 μm to 1500 μm, or 1 μm to 1,250 μm, or 1 μm to 1,000 μm, or 1 μm to 750 μm, or 1 μm to 500 μm, or 5 μm to 1,250 μm, or 5 μm to 1,000 μm, or 5 μm to 750 μm, or 10 μm to 5,000 μm, or 25 μm to 5,000 μm, or 50 μm to 5,000 μm, or 50 μm to 2,000 μm, or 50 μm to 1500 μm, or 50 μm to 1,250 μm, or 50 μm to 1,000 μm. In certain embodiments as otherwise described herein, the average pore size of the porous tube is within the range of 100 μm to 5,000 μm, e.g., 100 μm to 2,000 μm, or 100 μm to 1500 μm, or 100 μm to 1,250 μm, or 100 μm to 1,000 μm, or 250 μm to 5,000 μm, or 250 μm to 2,000 μm, or 250 μm to 1500 μm, or 250 μm to 1,250 μm, or 250 μm to 1,000 μm. In certain embodiments as otherwise described herein, the functional pore size of the porous tube is within the range of 500 μm to 5,000 μm, e.g., 500 μm to 2,000 μm, or 500 μm to 1500 μm, or 500 μm to 1,250 μm, or 500 μm to 1,000 μm, or 1,000 μm to 5,000 μm, or 1,000 μm to 2,000 μm, or 1,000 μm to 1500 μm. As used herein, average pore size is measured via capillary flow porometry in cases where pores are too small for convenient optical measurement. The person of ordinary skill in the art will recognize that a pore size within the range of 1 μm to 5,000 μm can be about equivalent to or larger than the size of most cells. However, the present inventors have determined that the porous tube can advantageously facilitate culture media perfusion at a desirable flow rate without appreciably disturbing and/or diminishing the count of cultured cells, especially when used with an outer filter layer.

The porous tube can have a porosity within a broad range; the person of ordinary skill in the art will select a porosity that provides a desired combination of mechanical stability and flow rate. In certain embodiments as otherwise described herein, the porous tube has a porosity within the range of 10% to 90%. The person of ordinary skill in the art will appreciate that porosity, a measure of the volume of pores in an article relative to the total volume of the material, can be measured by a number of known porosimetry methods; as used herein, water evaporation is used to measure porosity of the tube in cases where pores are too small for convenient optical measurement. In certain embodiments as otherwise described herein, the porosity of the porous tube is within the range of 20% to 90%, or 30% to 90%, or 40% to 90%, or 50% to 90%, or 10% to 80%, or 10% to 70%, or 10% to 60%, or 10% to 50%, or 20% to 80%, or 30% to 70%, or 40% to 60%.

Porosity of the porous tube can be provided by any of a number of art-recognized methods, e.g., molding, thermal perforation, laser drilling, electron beam drilling, electrical discharge machining, mechanical drilling, stamping or cutting.

In certain desirable embodiments as otherwise described herein, a majority of the porosity of the first porous tube is localized on a surface (e.g., a semicylinder surface) opposite the second liquid-permeable tube. Advantageously, the present inventors have determined that orientation of the porosity of the tube away from the second liquid-permeable tube can further minimize disturbance and/or diminishment of cultured cells effected by culture media perfusion from the second liquid-permeable tube to the first liquid-permeable tube. Accordingly, in certain embodiments as otherwise described herein, at least 65%, or at least 75%, or at least 85%, or at least 90% of the porosity of the first porous tube is localized on a surface (e.g., a semicylinder surface) opposite the second liquid-permeable tube.

In certain desirable embodiments as otherwise described herein, the porosity of the first porous tube is distributed relatively uniformly along an axis of the central lumen of the liquid-permeable tube, i.e., to facilitate uniform perfusion along the major axis of the bag.

As described above, the first tube can include a first outer filter layer disposed about the first inner support structure. The first outer filter layer is formed of a porous material that has an average pore size that is selected to help prevent cells from escaping the bag during perfusion. In certain embodiments, the average pore size is selected to be smaller than the average size of the cells to be grown in the bag. However, in other embodiments, the average pore size can be larger than the average size of the cells to be grown in the bag; the present inventors have determined that even larger-pore materials, arranged as described herein, can provide resistance to flow of cells through the first outer filter layer and out of the first tube, e.g., by providing a flow dynamic that keeps the cells from pushing strongly against the first outer filter layer. In certain embodiments as otherwise described herein, the first outer filter layer has an average pore size of less than 50 µm, e.g., less than 20 µm. In certain embodiments as otherwise described herein, the first outer filter layer has an average pore size of less than 10 µm. For example, in certain embodiments as otherwise described herein, the average pore size of the first outer filter layer is less than 5 µm, or less than 3 µm, or less than 2 µm. The person of ordinary skill in the art will recognize that a pore size of 10 µm or less can be about equivalent to or smaller than most cells (depending on the cell)—surprisingly, the present inventors have determined that the combination of the outer filter layer (e.g., having a small functional pore size relative to cultured cells) and the inner support structure (e.g., having a large functional pore size or spacing relative to cultured cells) can facilitate perfusion of culture media at a desirable flow rate without appreciably disturbing and/or diminishing the count of cultured cells. But even when the filter pore size is somewhat larger than the cell size, the filter can be effective in preventing significant loss of cells from the interior volume during perfusion.

In certain desirable embodiments, the first outer filter layer has an average pore size and/or a D99 pore size of less than about 100%, e.g., less than about 75%, or less than about 50%, or less than about 40%, or less than about 30%, or less than about 25% of the average diameter of a cultured cell type within the bag. For example, the present inventors have determined that an average pore size of the first outer filter layer of less than 10 µm, e.g., 5 µm, less than 3 µm, or even less than 2 µm, can advantageously help to retain mesenchymal stem cells (e.g., having an average diameter of about 10-13 µm) during perfusion. In another example, the present inventors have determined that an average pore size of the first outer filter layer of less than 1 µm, less than 600 nm or even less than 500 nm can advantageously help to retain red blood cells (e.g., having an average diameter of about 2-3 µm) during perfusion. But, as noted above, even in cases where the filter pore size is somewhat larger than the cell size, the filter can be effective in preventing significant loss of cells from the interior volume during perfusion, especially depending on the positioning of the first and second ports and tubes within the interior volume.

The person of ordinary skill in the art will appreciate that the "functional" pore size of a filter layer depends on both the average size and maximum size of the pores within the layer. Accordingly, in certain desirable embodiments as otherwise described herein, the D99 pore size of the filter layer (i.e., size of the pore that is at the 99th percentile in size) differs from the average pore size of the filter layer by at most 100%, e.g., at most 50%, at most 30%, or at most 10%. In certain desirable embodiments as otherwise described herein, the D99 pore size of the filter layer is less than 50 µm, e.g., less than 20 µm. In certain embodiments as otherwise described herein, the first outer filter layer has a D99 pore size of less than 10 µm. For example, in certain embodiments as otherwise described herein, the D99 pore size of the first outer filter layer is less than 5 µm, or less than 3 µm, or less than 2 µm.

However, as the person of ordinary skill in the art will appreciate, a small average pore size of the first outer filter layer can slow down flow through the bag. Accordingly, the person of ordinary skill in the art can select a pore size that is small enough to provide filtration for the desired cell type but large enough to provide a desired flow rate through the bag. For example, in certain embodiments as otherwise described herein, the average pore size of the first outer filter layer is at least 200 nm, e.g., at least 400 nm, at least 750 nm, or even at least 1000 nm. For example, in certain embodiments, the average pore size of the first outer filter layer is in the range of 1-10 µm, e.g., 1-7 µm, or 2-10 µm, or 2-7 µm.

And as described above, even when the average pore size is larger than the cell size, the arrangements described herein can help prevent flow of cells through the first tube. Use of a larger average pore size can also help improve flow rate through the system. Accordingly, in certain embodiments, the average pore size of the first outer filter layer is in the range of 5 microns to 50 microns, e.g., in the range of 5 microns to 20 microns, or 10 microns to 50 microns, or 10 microns to 30 microns.

In certain desirable embodiments as otherwise described herein, the first outer filter layer comprises (e.g., is formed of) a polymer having a total organic carbon in water of less than 0.1 mg/cm². In certain embodiments as otherwise described herein, the first outer filter layer comprises polyester or polyether sulfone. Other suitable materials include PVDF, nylon, and hydrophilic PTFE.

However, in other embodiments of the bags as otherwise described herein, the first tube does not include a filter layer separate from a support structure, but instead is a tube that has an average pore size as described herein for the first outer filter layer. This can be made, for example, by forming porous film material into a tube (e.g., by welding), or by providing a rigid tubular material with the desired pore size. In certain embodiments as otherwise described herein, the first tube has an average pore size of less than 50 µm, e.g., less than 20 µm. For example, in certain embodiments as otherwise described herein, the average pore size of the first tube is less than 10 µm, e.g., less than 5 µm, or less than 3 µm, or less than 2 µm. In certain desirable embodiments, the first tube has an average pore size and/or a D99 pore size of less than about 100%, e.g., less than about 75%, or less than about 50%, or less than about 40%, or less than about 30%, or less than about 25% of the average diameter of a cultured cell type within the bag, e.g., as described above with respect to the first outer filter layer. In certain desirable embodiments as otherwise described herein, the D99 pore size of the first tube (i.e., size of the pore that is at the 99$^{th}$ percentile in size) differs from the average pore size of the tube by at most 50%, e.g., at most 30%, or at most 10%. In certain desirable embodiments as otherwise described herein, the D99 pore size of the first tube is less than 50 µm, e.g., less than 20 µm. In certain embodiments as otherwise described herein, the first tube has a D99 pore size of less than 10 µm. For example, in certain embodiments as otherwise described herein, the D99 pore size of the first tube is less than 5 µm, or less than 3 µm, or less than 2 µm. In certain embodiments as otherwise described herein, the average pore size of the first tube is at least 200 nm, e.g., at least 400 nm, at least 750 nm, or even at least 1000 nm. In certain embodiments as otherwise described herein, the average pore size of the first tube is in the range of 5 microns to 50 microns, e.g., in the range of 5 microns to 20 microns, or 10 microns to 50 microns, or 10 microns to 30 microns. In certain desirable embodiments, the first tube is rigid, i.e., sufficiently rigid to maintain its cross-sectional shape without pressure of a fluid flowing therethrough.

As the second liquid-permeable tube (e.g., tube 180 of FIG. 1) is generally used to input media into the interior compartment of the bag, in many embodiments it need not have a filter layer. Thus, in certain embodiments, the second liquid-permeable tube can be as described above for the porous tube support structure of the first liquid-permeable tube, without an outer filter layer. The second liquid-permeable tube can take a variety of other tubular structures.

Figure 3:
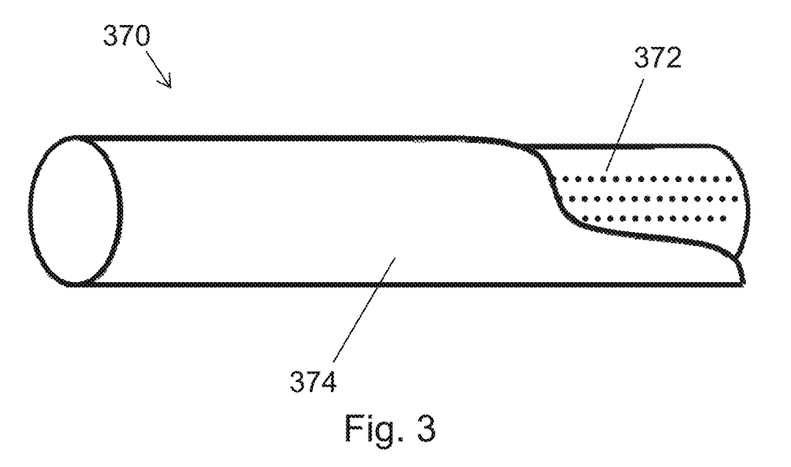
FIG. 3 is a schematic cutaway view of a liquid-permeable tube according to one embodiment of the disclosure.

However, in other embodiments as otherwise described herein, the second liquid-permeable tube comprises a second inner support structure defining a central lumen of the tube and a second outer filter layer surrounding the second inner support structure. And in other embodiments, the second liquid-permeable tube is a tube having an average pore size of no more than 50 microns. In such embodiments, the second liquid-permeable tube can be as otherwise described in any embodiment herein for the first liquid-permeable tube. Advantageously, such bags allow for media flow as described above—from the second tube, through the interior volume, and out of the first tube—as well as the reverse. The present inventors have determined that cells can be cleared from the first outer filter layer, but retained within the interior compartment, by reversing the direction of perfusion in such embodiments. Of course, such "bi-directional" bags can also facilitate more convenient set-up and operation by a user. In certain desirable embodiments, the inner support structure and outer filter layer of the second liquid-permeable tube are as described herein with respect to any embodiment the first liquid-permeable tube. Structures as shown in FIGS. 2 and 3 can in certain embodiments be used as the second liquid-permeable tube.

For example, in certain embodiments as otherwise described herein, the second inner support structure comprises a spiral-wound filament (e.g., a spiral-wound filament described above). In certain such embodiments, the first inner support structure of the first liquid-permeable tube also comprises a spiral-wound filament. Similarly, in certain other embodiments as otherwise described herein, the second inner support structure comprises a frame structure. In certain such embodiments, the first inner support structure of the first liquid-permeable tube also comprises a frame structure In another example, in certain embodiments as otherwise described herein, the second inner support structure comprises a porous tube (e.g., a porous tube as described above). For example, in certain embodiments as otherwise described herein, the first inner support structure comprises a first porous tube and the second inner support structure comprises a second porous tube. In certain such embodiments, the second porous tube (e.g., and the first porous tube) has a functional pore size in the range of 1 µm to 5,000 µm, e.g., 1 µm to 1,000 µm, or 100 µm to 5,000 µm, or 500 µm to 5,000 µm. In certain such embodiments, the second porous tube (e.g., and the first porous tube) has a porosity in the range of 10% to 90%, or 20% to 80%, or 30% to 70%. In certain such embodiments, at least 60%, or at least 75%, or at least 90% of the porosity of the second porous tube is localized on a surface (e.g., a semicylinder surface) opposite the first liquid-permeable tube (e.g., and at least 60%, or at least 75%, or at least 90% of the porosity of the first porous tube is localized on a surface (e.g., a semicylinder surface) opposite the second liquid-permeable tube). In certain embodiments, the second porous tube (e.g., and the first porous tube) comprises a silicone elastomer. In certain embodiments, the second outer filter layer (e.g., and the first outer filter layer) has an average pore size of less than 10 µm, e.g., less than 5 µm, or less than 3 µm, or less than 2 µm. In certain embodiments as otherwise described herein, the average pore size of the second outer filter layer is at least 200 nm, e.g., at least 400 nm, at least 750 nm, or even at least 1000 nm. In certain embodiments, the second outer filter layer (e.g., and the first outer filter layer) comprises polyester or polyethersulfone.

And in other embodiments, the second liquid-permeable tube is a tube that does not include a second support structure and a second outer filter layer, but instead is in the form of a tube having a pore size as described herein for the second outer filter layer. This can be made, for example, by forming porous film material into a tube (e.g., by welding), or by providing a rigid tubular material with the desired pore size. In certain embodiments as otherwise described herein, the second tube has an average pore size of less than 50 µm, e.g., less than 20 µm. For example, in certain embodiments as otherwise described herein, the average pore size of the second tube is less than 10 µm, e.g., less than 5 µm, or less than 3 µm, or less than 2 µm. In certain desirable embodiments, the second tube has an average pore size and/or a D99 pore size of less than about 100%, e.g., less than about 75%, or less than about 50%, or less than about 40%, or less than about 30%, or less than about 25% of the average diameter of a cultured cell type within the bag, e.g., as described above with respect to the first outer filter layer. In certain desirable embodiments as otherwise described herein, the D99 pore size of the second tube (i.e., size of the pore that is at the 99th percentile in size) differs from the average pore size of the second tube by at most 50%, e.g., at most 30%, or at most 10%. In certain embodiments as otherwise described herein, the average pore size of the second tube is at least 200 nm, e.g., at least 400 nm, at least 750 nm, or even at least 1000 nm. In certain desirable embodiments, the second tube is rigid, i.e., sufficiently rigid to maintain its cross-sectional shape without pressure of a fluid flowing therethrough.

In cases where the second liquid-permeable tube is covered by a second filter layer or has a small pore size as described above, then it can be desirable for the third port to be present to simplify the introduction of cells into and/or the removal of cells from the interior volume of the bag.

As used herein, total organic carbon (TOC) is the amount of carbon bound in an organic compound and is often used as a non-specific indicator of pharmaceutical manufacturing equipment, among other things. Total organic carbon is utilized as a process control attribute in the biotechnology industry to monitor the performance of unit operations that employ purification and distribution systems.

Total organic carbon is measured by extraction from an internal surface area of a container or the surface area of another item (with results provided in units of mg/cm$^2$, the total extractable organic carbon per square centimeter of the surface area). A material is extracted by being contacted by a given volume of purified water at 70° C. for 24 hours.

One example of the total organic carbon value of a fluorinated ethylene propylene container (i.e., using FEP films) is <0.01 mg/cm$^2$. For silicone tubing, extraction ratios may be 14.6 cm$^2$/mL (e.g., Biosil) or may be 15.9 cm$^2$/mL (e.g., SR139), and one example of the total organic carbon value of a silicone Biosil tube is 0.021 mg/cm$^2$, and one example of the total organic carbon value of silicone SR139 tubing is 0.008 mg/cm$^2$. For at least certain silicone tubing, the samples may be diluted, as the volume and concentration of the extraction cause the value to be above the maximum detection of the machine. The dilution and different extraction ratio requires the comparison of these samples with bag samples to provide a weight/area value.

One example of the total organic carbon value of a thermoplastic elastomer (TPE) is 0.002 mg/cm$^2$. One example of the total organic carbon value of a fluorinated ethylene propylene is 0.00005 mg/cm$^2$. One example of the total organic carbon value of a silicone is 0.021 mg/cm$^2$. One example of the total organic carbon value of a PMP film is 0.00001 mg/cm$^2$. An example of the total organic carbon value of a historically used cell culture bag is 0.002 mg/cm$^2$ of interior wetted surface of the article (0.032 mg/g of article).

As quantified herein, total organic carbon is measured according to US Pharmacopeia (USP) 643 using equipment that utilizes a high temperature wet oxidation reaction of UV-promoted chemical oxidation (Ultra-Clean Technology Handbook: Volume 1: Ultra-Pure Water, Ohmi, Tadahiro; CRC Press, 1993, pp. 497-517). Purified water is placed in contact with the polymer for 24 hours at 70° C., at a ratio of 3 cm$^2$ of article surface area to 1 mL of water. The water is removed from contact with the polymer and tested in a TOC analyzer. A suitable piece of equipment is a TEKMAR DOHRMANN Model Phoenix 8000 TOC analyzer.

In certain embodiments as otherwise described herein, each of the polymer films making up the bag (e.g., film 110 and film 120 of FIG. 1) are gas-permeable and comprise a polymer having a total organic carbon in water of less than 0.1 mg/cm$^2$.

For example, in certain embodiments as otherwise described herein, each of the polymer films making up the bag comprises (or is formed of) a polymer having a total organic carbon in water of less than 1 mg/cm$^2$, or 0.9 mg/cm2, or 0.8 mg/cm$^2$, or 0.7 mg/cm$^2$, or 0.6 mg/cm$^2$, or 0.5 mg/cm$^2$, or 0.4 mg/cm$^2$, or 0.3 mg/cm$^2$, or 0.2 mg/cm$^2$, or 0.1 mg/cm$^2$, or 0.09 mg/cm$^2$, or 0.08 mg/cm$^2$, or 0.07 mg/cm$^2$, or 0.06 mg/cm$^2$, or 0.05 mg/cm$^2$, or 0.04 mg/cm$^2$, or 0.03 mg/cm$^2$, or 0.02 mg/cm$^2$, or 0.01 mg/cm$^2$, or 0.009 mg/cm$^2$, or 0.008 mg/cm$^2$, or 0.007 mg/cm$^2$, or 0.006 mg/cm$^2$, or 0.005 mg/cm$^2$, or 0.004 mg/cm$^2$, or 0.003 mg/cm$^2$, or 0.002 mg/cm$^2$, or 0.001 mg/cm$^2$.

For example, in certain embodiments as otherwise described herein, each of the polymer films making up the bag comprises (or is formed of) a polymer having a total organic carbon in water within the range of 0.001 mg/cm$^2$ to 0.1 mg/cm$^2$, or 0.001 mg/cm$^2$ to 0.095 mg/cm$^2$, or 0.001 mg/cm$^2$ to 0.075 mg/cm$^2$, or 0.001 mg/cm$^2$ to 0.05 mg/cm2, or 0.001 mg/cm$^2$ to 0.01 mg/cm$^2$, or 0.001 mg/cm$^2$ to 0.005 mg/cm$^2$, or 0.001 mg/cm$^2$ to 0.025 mg/cm$^2$. In certain embodiments as otherwise described herein each of the polymer films making up the bag comprises (or is formed of) a polymer having a total organic carbon in water is within the range of 0.01 mg/cm$^2$ to 0.1 mg/cm$^2$, or 0.01 mg/cm$^2$ to 0.075 mg/cm$^2$, or 0.01 mg/cm$^2$ to 0.05 mg/cm$^2$, or 0.01 mg/cm$^2$ to 0.025 mg/cm$^2$. In certain embodiments, each of the polymer films making up the bag comprises (or is formed of) a polymer having a total organic carbon in water within the range of 0.05 mg/cm$^2$ to 0.1 mg/cm$^2$, or 0.05 mg/cm$^2$ to 0.09 mg/cm$^2$, or 0.05 mg/cm$^2$ to 0.075 mg/cm$^2$, or 0.05 mg/cm$^2$ to 0.06 mg/cm$^2$. In certain embodiments, each of the first polymer film and the second polymer film comprise a polymer having a total organic carbon in water within the range of 0.005 mg/cm$^2$ to 0.1 mg/cm$^2$, 0.005 mg/cm$^2$ to 0.095 mg/cm$^2$, 0.005 mg/cm$^2$ to 0.075 mg/cm$^2$, 0.005 mg/cm$^2$ to 0.05 mg/cm$^2$, 0.005 mg/cm$^2$ to 0.025 mg/cm$^2$, or 0.005 mg/cm$^2$ to 0.01 mg/cm2.

In certain embodiments as otherwise described herein, each of the polymer films making up the bag (e.g., film 110 and film 120 of FIG. 1) comprises (or is formed of) an elastomer, a fluoropolymer, polymethylpentene, or any combination thereof. For example, in certain embodiments as otherwise described herein each of the first polymer film and the second polymer film comprise (e.g., are) natural polyisoprene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), cyclic olefin copolymers, polyolefin elastomers, elastomeric PET, or mixtures thereof.

The person of ordinary skill in the art will appreciate that elastomers are polymers with viscoelastic properties, low crystallinity, and high amorphous content, generally having low Young's modulus and high elongation at break compared to other materials. The term elastomers may be used interchangeably with the term rubber, although rubber is preferred when referring to vulcanisates. Elastomers are amorphous polymers constructed from monomers of carbon, hydrogen, oxygen, and/or silicon.

Thermoplastic polyurethanes (TPUs) are known in the art. Typically, a thermoplastic polyurethane is formed by reacting a polyol with an isocyanate. The overall properties of the polyurethane will depend upon the type of polyol and isocyanate, crystallinity in the polyurethane, the molecular weight of the polyurethane and chemical structure of the polyurethane backbone.

The person of ordinary skill in the art will appreciate that polyurethanes may be either thermoplastic or thermoset, depending on the degree of crosslinking present. Thermoplastic urethanes (TPUs) do not have primary crosslinking while thermoset polyurethanes have a varying degree of crosslinking, depending on the functionality of the reactants.

Thermoplastic polyurethanes are commonly based on either methylene diisocyanate (MDI) or toluene diisocyanate (TDI) and include both polyester and polyether grades of polyols. Thermoplastic polyurethanes can be formed by a "one-shot" reaction between isocyanate and polyol or by a "pre-polymer" system, wherein a curative is added to the partially reacted polyolisocyanate complex to complete the polyurethane reaction. Examples of some common thermoplastic polyurethane elastomers based on "pre-polymers" are "TEXIN", a tradename of Bayer Materials Science, "ESTANE", a tradename of Lubrizol, "PELLETHANE", a tradename of Dow Chemical Co., and "ELASTOLLAN", a tradename of BASF, Inc.

GENIOMER® thermoplastic silicones include, but are not limited to GENIOMER® 140 Silicone TPE, GENIOMER® 200 Silicone TPE Elastomer (90% polydimethylsiloxane and isocyanate), GENIOMER®, 60 Silicone TPE, GENIOMER® 80 Silicone TPE and GENIOMER® 145 TPE, all of which comprise 90% polydimethylsiloxane and isocyanate.

Of course, other configurations of thermoplastics (elastomer and non-elastomer) and fluoropolymer configurations could also be used to control the gas permeability of a composite, whilst containing a low TOC fluid contact layer. Control of gas permeability could be for the purpose of either creating a high or low gas permeable composite. Examples of thermoplastics elastomers (TPE) include styrene block copolymers (TPE-s), olefins (TPE-o), alloys (TPE-v or TPV), polyurethanes (TPU), copolyesters, and polyamides. Examples of non-elastomer thermoplastics include acrylics, acrylonitrile butadiene styrene (ABS), nylon, polylactic acid (PLA), polybenzimidazole (PBI), polycarbonate (PC), polyether sulfone (PES), polyetherether ketone (PEEK), polyetherimide (PEI), polyethylene (PE), polyphenylene oxide (PPO), polyphenylene sulfide (PPS), polypropylene (PP), polystyrene (PS), and polyvinyl chloride (PVC), ethylene vinyl alcohol (EVOH), as well as any traditionally rigid polymer whose monomer architecture has been modified to reduce crystallinity and increase flexibility.

In certain embodiments as otherwise described herein, each of the first polymer film and the second polymer film comprise (e.g., are) a fluoropolymer. For example, in certain such embodiments, each of the first polymer film and the second polymer film comprise (e.g., are) FEP (fluorinated ethylene propylene), TFE (tetrafluoroethylene), PFA (perfluoroalkoxyalkane), PVF (polyvinylfluoride), PVDF (polyvinylidene fluoride), PTFE (polytetrafluoroethylene), 3M™ Dyneon™ TFM™ modified PTFE, PCTFE (polychlorotrifluoroethylene), HTE (tetrafluoroethylene/hexafluoropropylene/ethylene copolymer), ETFE (polyethylenetetrafluoroethylene), ECTFE (polyethylenechlorotrifluoroethylene), FFPM/FFKM (perfluoroelastomer), FPM/FKM (chlorotrifluoroethylene/vinylidene fluoride copolymer), PFPE (perfluoropolyether), MFA (tetrafuoroethylene and perfuoromethyl vinyl-ether copolymer), CTFE/VDF (chlorotrifuoroethylene-vinylidene fluoride copolymer), TFE/HFP (tetrafuoroethylene-hexafuoropropylene copolymer), chlorotrifluoroethylene/hexafluoropropylene, THV (hexafluoropropylene/tetrafluoroethylene/vinylidene copolymer), perfluoro(1-butenyl vinyl ether) homocyclopolymer having functionalized polymer-end groups, or mixtures thereof.

In certain embodiments, the first and second polymer film comprise PMP (polymethylpentene), a thermoplastic polymer of methylpentene monomer units. It has been used for gas permeable packaging, autoclavable medical and laboratory equipment, microwave components, and cookware. It is commercially available as TPX™ from Mitsui Chemicals America, Inc., Rye Brook, NY.

In certain embodiments, the first polymer film and second polymer film of a bag as otherwise described herein comprise a single layer of an elastomer, such as a thermoplastic silicone (e.g. GENIOMER® by Wacker Chemie AG, a polydimethylsiloxane/urea copolymer) or a fluoropolymer with TOC and permeability properties as described herein.

In other embodiments, each of the polymer films making up the bag comprises (or is formed of) a laminate including materials described herein. For example, in certain embodiments as otherwise described herein, each of the polymer films making up the bag (e.g., film 110 and film 120 of FIG. 1) comprises (or is formed of) comprise an inner layer including a fluoropolymer (e.g., fluorinated ethylene propylene) and an outer layer including a silicone elastomer, the inner layer of each film forming the interior compartment of the bag (e.g., interior compartment 130) and the outer layer of each film forming the exterior surface of the bag. Such materials are described, e.g., in U.S. Pat. No. 9,926,524, which is hereby incorporated herein by reference in its entirety.

In certain embodiments as otherwise described herein, at least one of (e.g., each of) the polymer films making up the bag has a gas permeability (e.g., oxygen permeability) of at least 100 cc/m$^2$ per day, preferably at least 500 cc/m$^2$ per day, or preferably at least 1,000 cc/m$^2$ per day, or at least 1,500 cc/m$^2$ per day, or at least 2,000 cc/m$^2$ per day, or even at least 2,200 cc/m$^2$ per day. For example, in certain embodiments as otherwise described herein, each of the polymer films making up the bag comprises (or is formed of) an elastomer fluoropolymer composite and have gas permeability (e.g., oxygen permeability) of at least 100 cc/m$^2$ per day, or at least 500 cc/m$^2$ per day, or at least 1,000 cc/m$^2$ per day, or at least 1,500 cc/m$^2$ per day, or at least 2,000 cc/m$^2$ per day, or even at least 2,200 cc/m$^2$ per day. In certain embodiments, at least one of (e.g., each of) the polymer films making up the bag has a gas permeability in the range of 1000-25000 cc/m$^2$ per day. Oxygen permeability is measured with a MOCON Ox-tran 2/21H Oxygen Analyzer, following ASTM D3985, at 25° C. In another aspect of film permeability, normalized units (cc-mm/m$^2$-day) can be used to show a film of any thickness. For example, the converted range for a 5 mm film would be from about 12.7 cc-mm/m$^2$-day to at least about 279 cc-mm/m$^2$-day at a temperature of 25° C. The permeability of the construct/composite can be expressed in cc/m$^2$ terms, as it would be comprised of two layers.

Similarly, each of the first and second fluid-permeable tubes can be made from low-TOC materials. In certain embodiments as otherwise described herein, each of the first tube and the second tube is formed of polymers having a total organic content of less than 0.1 mg/cm$^2$, e.g., less than 0.09 mg/cm$^2$, or 0.08 mg/cm$^2$, or 0.07 mg/cm$^2$, or 0.06 mg/cm$^2$, or 0.05 mg/cm$^2$, or 0.04 mg/cm$^2$, or 0.03 mg/cm$^2$, or 0.02 mg/cm$^2$, or 0.01 mg/cm$^2$, or 0.009 mg/cm$^2$, or 0.008 mg/cm$^2$, or 0.007 mg/cm$^2$, or 0.006 mg/cm$^2$, or 0.005 mg/cm$^2$, or 0.004 mg/cm$^2$, or 0.003 mg/cm$^2$, or 0.002 mg/cm$^2$, or 0.001 mg/cm$^2$.

Figure 4:
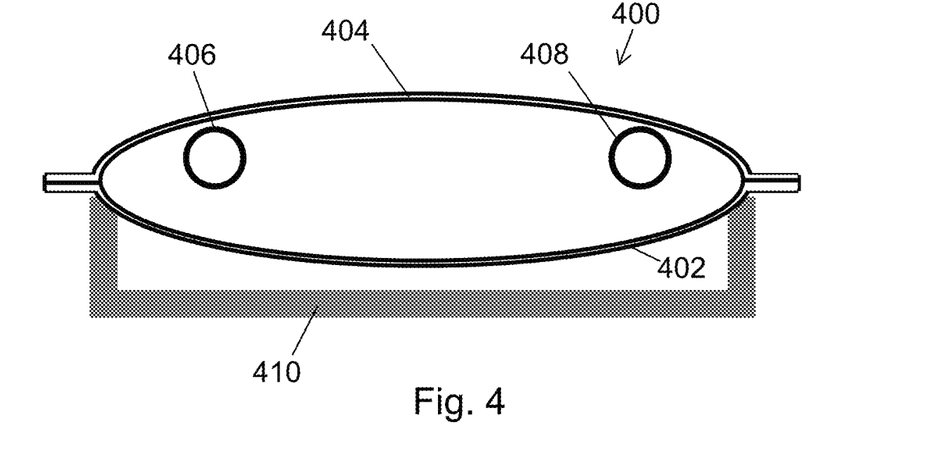
FIG. 4 is a schematic cross-sectional view of a cell culture system according to one embodiment of the disclosure.

The bags described herein are especially useful in cell culture systems. Accordingly, another aspect of the disclosure is a cell culture system comprising a bag as described herein. An embodiment of such a system is shown in cross-sectional view in FIG. 4. Bag 400, formed from a first polymer film 402 and a second polymer film 404, is oriented on a support 410 such that a first liquid permeable tube 406 and a second liquid-permeable tube 408 are elevated relative to a majority of first polymer film 402. Another embodiment of such a system is shown in cross-sectional view in FIG. 5.

Figure 5:
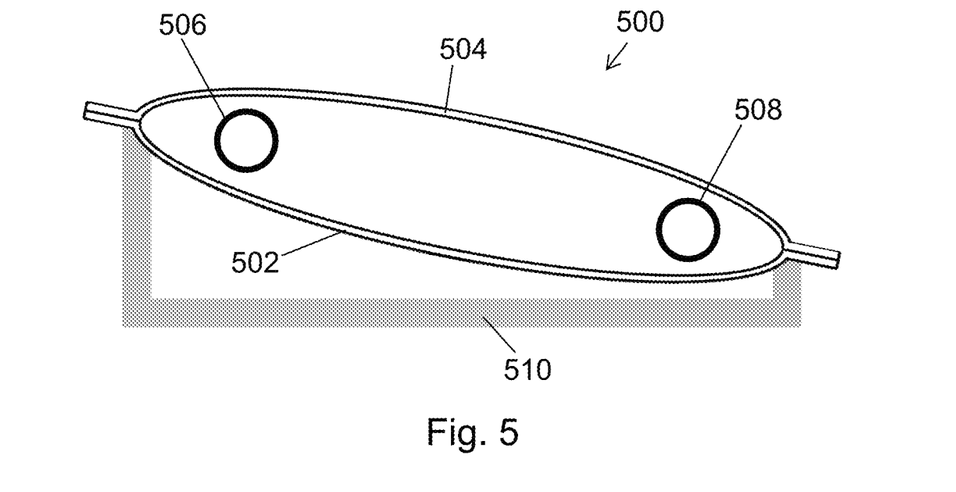
FIG. 5 is a schematic cross-sectional view of a cell culture system according to one embodiment of the disclosure.

Bag 500, formed from a first polymer film 502 and a second polymer film 504, is oriented on a support 510 such that a first liquid-permeable tube 506 is elevated relative to a second liquid-permeable tube 508. This allows for cells to collect on the lower surface of the bag (oriented as shown) with a lower degree of disturbance from fluid flow in the region of the tubes.

As noted above, the present inventors have determined that the bags and systems described herein are useful for perfusing media through a cell culture. Accordingly, another aspect of the disclosure is a method for cultivating cells that includes providing a bag or system as otherwise described herein (e.g., bag 100 of FIG. 1), including media and cells in the interior compartment (e.g., interior compartment 130), and flowing media through the interior compartment by adding media through the second port (e.g., port 150) and through the second liquid-permeable tube (e.g., tube 180), and removing media through the first liquid-permeable tube (e.g., tube 170) and through the first port (e.g., port 140). In certain such embodiments, the bag or system including media and cells in the interior compartment can be provided by adding media and cells to the bag through a third port formed in an exterior surface of the bag and in fluid communication with the interior compartment of the bag (e.g., port 160 of bag 100 of FIG. 1). A variety of flow rates can be used, for example, in the range of 0.5-20 mL/min; the flow rate is desirably low enough to allow cells to be maintained at the bottom of the bag through gravitational settling. Of course, over the course of normal operation, flow rates can vary, or can even be discontinuous (e.g., incidentally, or based on cell activity). Accordingly, in another example, the flow rate can in the range of 0.2-2 bag volume replacements per day. The bag can be maintained at a desired incubation temperature during the perfusion, and can be rocked or otherwise agitated.

When a third port is included, cultivated cells can be removed from the interior compartment through the third port. Cultivated cells can otherwise be removed, e.g., through the second port.

In certain embodiments, the method further includes, after flowing media through the interior compartment by adding media through the second port and through the second liquid-permeable tube and removing media through the first liquid-permeable tube and through the first port, reversing the direction of flow by flowing media through the interior compartment by adding media through the first port and through the first liquid-permeable tube and removing media through the second liquid-permeable tube and through the second port. This can help flush cells or any other particulate from the first outer filter layer. Such embodiments can be especially advantageous when the bag includes a second outer filter layer or a small-pore porous second tube as described above. However, even in other constructions, a short reversal of flow can flush the first outer filter layer without significantly drawing cells through the second tube.

In an example, a perfusion bag was constructed using a three-port 160 mL VueLife cell culture bag formed from 5-mil FEP films. Perforated (~3 mm holes) FEP tubes having an outer diameter of 0.25 in. and an inner diameter of 0.1875 in. and a length of 8 in., fit with polyester filters having a functional pore size of 6 μm, were inserted into the first and third ports of the bag, and the ports were collar-sealed around the tubes. Tubing was connected to the second port and to the first and second tubes, and a source bag was connected to the second tube and a waste bag to the first tube.

In the initial configuration for basic flow evaluation, the source bag was filled, elevated with respect to the test bag, and tilted slightly. The test bag was disposed in a mesh cartridge to constrain its thickness, and then flow of red-dyed water from the source bag was initiated. Under the force of gravity, with no manual assistance required, media filled the test bag and began to move into the waste bag, with no noticeable delay caused by the filters. The tubing between the test and waste bags (e.g., tube 604) was then placed in A Watson-Marlow pump. The system performed well over the tested range of speeds from 2 to 10 rpm (for the tubing used, this corresponds to a nominal 0.9 to 4.7 mL/min flow rate, according to the manufacturer's performance advice). The system was allowed to run for about an hour at 6 rpm (2.8 mL/min), apparently achieving a stable steady state. The source bag of red-dyed water was replaced by a source bag of blue-dyed water, without draining the test bag. Perfusion was performed at 6 rpm. While the advancing front of blue-dyed water was not perfectly uniform along the bag, it did replace all of the red-dyed water with no dead spots. The advance of the blue-dyed water appeared to be influenced by ripples in the bag film (as is typical in an autoclaved bag) and the substantial presence of air in the bag; these and not the use of the fluid-permeable tubes appeared to be the dominant factors. Accordingly, the use of the fluid-permeable tubes as described herein can provide efficient perfusion of the internal compartment of the bag.

Human T cells were harvested after 10 days of expansion in TexMACS™ medium supplemented with recombinant IL-2 in a VueLife 290-C bag. T cells were seeded at a density of $0.5 \times 10^6$ cells/mL into the test bag in 160 mL of Tex-MACS™ medium and cultured with perfusion for 24 hours at 37 C, 5% CO2, ambient oxygen. After the 24-hour culture period, a cell culture sample was collected from the ALN 2 bag via the third port and analyzed for cell count and viability. As shown in the table below, cell viability remained high at 90.9%, and cell numbers remained stable. In addition, the bag was massaged to ensure homogenous cell distribution and potential harvest of cells attached to the filters in the test samples used for cell counting. Three samples were analyzed, and showed equal numbers for cell count and viability measurements.

|  | Start of culture | After 24 h (perf.) | After 72 h (no perf.) |
| --- | --- | --- | --- |
| Viability | 88.0% | 90.9% | 85.80% |
| Viable cells [×10$^6$] | 50 | 77.92 | 55.8 |
| Total cells [×10$^6$] | 50 | 85.6 | 65.12 |

Imaging of cell distribution in the bag revealed that cells were homogenously dispersed throughout the bag, and were also found near/on both filters. No cells were found in either the upstream media bag or the downstream waste bag, suggesting that the filters were efficient at retaining the cell population inside the interior volume of the test bag as intended. Microscopy of samples indicated that the cells had good morphology throughout the bag. The test bag was then placed back into culture (static culture; without perfusion) for another 48 h. After that, cells were once again analyzed for cell count, viability and morphology. Cell viability was 85.8%, and $55.8 \times 10^6$ viable cells were found to remain in the test bag. Cell morphology remained unchanged after the extended culture period, which indicates that the filter material was not immediately cytotoxic or affecting T cell fate in this system.

Various embodiments of the disclosure relate to the enumerated embodiments described below, which can be combined in any number and in any fashion that is not technically or logically inconsistent.

Embodiment 1

A bag comprising
one or more polymer films, having edges bonded together to form edges around an undivided interior compartment of the bag;
a first port formed in an exterior surface of the bag;
a first liquid-permeable tube extending into and in fluid communication with the interior compartment of the bag, the first tube being operatively coupled to the first port;
a second port formed in an exterior surface of the bag;
a second liquid-permeable tube extending into and in fluid communication with the interior compartment of the bag, the second tube being operatively coupled to the second port; and
optionally, a third port formed in an exterior surface of the bag, the third port being in fluid communication with the interior compartment of the bag;
wherein the first tube comprises a first inner support structure defining a central lumen of the tube and a first outer filter layer surrounding the first inner support structure.

Embodiment 2

The bag of embodiment 1, wherein the one or more polymer films include a first polymer film and a second polymer film, having edges bonded together to form edges around an undivided interior compartment of the bag.

Embodiment 3

The bag of embodiment 1 or embodiment 2, wherein the first inner support structure comprises a spiral-wound filament.

Embodiment 4

The bag of embodiment 1 or embodiment 2, wherein the first inner support structure comprises a first porous tube.

Embodiment 5

The bag of embodiment 4, wherein the first porous tube has an average pore size in the range of 1 μm to 5,000 μm (e.g., 25 μm to 1,000 μm, or 50 μm to 5,000 μm).

Embodiment 6

The bag of embodiment 4, wherein the first porous tube has an average pore size in the range of 100 μm to 5,000 μm (e.g., 500 μm to 5,000 μm, or 1,000 μm to 5,000 μm).

Embodiment 7

The bag of any of embodiments 4-6, wherein the first porous tube has a porosity in the range of 10% to 90% (e.g., 30% to 70%).

Embodiment 8

The bag of any of embodiments 4-7, wherein at least 60% (e.g., at least 75%, or at least 90%) of the porosity of the first porous tube is localized on a surface (e.g., semicylindrical) opposite the second liquid-permeable tube.

Embodiment 9

The bag of any of embodiments 1-8, wherein the first porous tube is formed of a polymer.

Embodiment 10

The bag of any of embodiments 1-8, wherein the first porous tube comprises a fluoropolymer.

Embodiment 11

The bag of any of embodiments 1-10, wherein the first outer filter layer has an average pore size of less than 50 μm, e.g., less than 20 μm.

Embodiment 12

The bag of any of embodiments 1-10, wherein the first outer filter layer has an average pore size of less than 10 μm (e.g., less than 5 μm, or less than 3 μm, or less than 2 μm).

Embodiment 13

The bag of any of embodiments 1-12, wherein the first outer filter layer has an average pore size of at least 200 nm, e.g., at least 400 nm, at least 750 nm, or at least 1000 nm.

Embodiment 14

The bag of any of embodiments 1-13, wherein the D99 pore size of the first outer filter layer differs from the average pore size of the first outer filter layer by at most 50%, e.g., at most 30%, or at most 10%.

Embodiment 15

The bag of any of embodiments 1-14, wherein the first outer filter layer has a D99 pore size of less than 50 μm, e.g., less than 20 μm.

Embodiment 16

The bag of any of embodiments 1-14, wherein the first outer filter layer has a D99 pore size of less than 10 μm (e.g., less than 5 μm, or less than 3 μm, or less than 2 μm).

Embodiment 17

The bag of any of embodiments 1-16, wherein the first outer filter layer has an average pore size of at least 200 nm, e.g., at least 400 nm, at least 750 nm, or at least 1000 nm.

Embodiment 18

The bag of any of embodiments 1-10 and 14, wherein the average pore size of the first outer filter layer is in the range of 5 microns to 50 microns, e.g., in the range of 5 microns to 20 microns, or 10 microns to 50 microns, or 10 microns to 30 microns.

Embodiment 19

The bag of any of embodiments 1-10 and 14, wherein the first outer filter layer has an average pore size and/or a D99 pore size of less than about 100%, e.g., less than about 75%, or less than about 50%, or less than about 40%, or less than about 30%, or less than about 25% of the average diameter of a cultured cell type within the bag.

Embodiment 20

The bag of any of embodiments 1-19, wherein the first outer filter layer comprises polyester or polyethersulfone.

Embodiment 21

The bag of any of embodiments 1-20, wherein the second tube comprises a second inner support structure defining a central lumen of the tube and a second outer filter layer surrounding the second inner support structure Embodiment 22

The bag of embodiment 21, wherein the second inner support structure comprises a spiral-wound filament.

Embodiment 23

The bag of embodiment 21, wherein the second inner support structure comprises a second porous tube.

Embodiment 24

The bag of embodiment 23, wherein the second porous tube has an average pore size in the range of 1 µm to 5,000 µm (e.g., 25 µm to 1,000 µm, or 50 µm to 5,000 µm).

Embodiment 25

The bag of embodiment 23, wherein the second porous tube has an average pore size in the range of 100 µm to 5,000 µm (e.g., 500 µm to 5,000 µm, or 1,000 µm to 5,000 µm).

Embodiment 26

The bag of embodiment 24 or 25, wherein the second porous tube has a porosity in the range of 10% to 90% (e.g., 30% to 70%).

Embodiment 27

The bag of any of embodiments 23-26, wherein at least 60% (e.g., at least 75%, or at least 90%) of the porosity of the second porous tube is localized on a surface (e.g., semicylindrical) opposite the first liquid-permeable tube.

Embodiment 28

The bag of any of embodiments 23-27, wherein the second porous tube is formed of a polymer.

Embodiment 29

The bag of any of embodiments 23-27, wherein the second porous tube comprises a fluoropolymer.

Embodiment 30

The bag of any of embodiments 21-29, wherein the second outer filter layer has an average pore size of less than 50 µm, e.g., less than 20 µm.

Embodiment 31

The bag of any of embodiments 21-29, wherein the second outer filter layer has an average pore size of less than 10 µm (e.g., less than 5 µm, or less than 3 µm, or less than 2 µm).

Embodiment 32

The bag of any of embodiments 21-31, wherein the second outer filter layer has an average pore size of at least 200 nm, e.g., at least 400 nm, at least 750 nm, or at least 1000 nm).

Embodiment 33

The bag of any of embodiments 21-32, wherein the D99 pore size of the second outer filter layer differs from the average pore size of the second outer filter layer by at most 50%, e.g., at most 30%, or at most 10%.

Embodiment 34

The bag of any of embodiments 21-33, wherein the second outer filter layer has a D99 pore size of less than 50 µm, e.g., less than 20 µm.

Embodiment 35

The bag of any of embodiments 21-33, wherein the second outer filter layer has a D99 pore size of less than 10 µm (e.g., less than 5 µm, or less than 3 µm, or less than 2 µm).

Embodiment 36

The bag of any of embodiments 21-35, wherein the second outer filter layer has an average pore size of at least 200 nm, e.g., at least 400 nm, at least 750 nm, or even at least 1000 nm.

Embodiment 37

The bag of any of embodiments 21-30 and 35, wherein the average pore size of the second outer filter layer is in the range of 5 microns to 50 microns, e.g., in the range of 5 microns to 20 microns, or 10 microns to 50 microns, or 10 microns to 30 microns.

Embodiment 38

The bag of any of embodiments 21-39 and 33, wherein the second outer filter layer has an average pore size and/or a D99 pore size of less than about 100%, e.g., less than about 75%, or less than about 50%, or less than about 40%, or less than about 30%, or less than about 25% of the average diameter of a cultured cell type within the bag.

Embodiment 39

The bag of any of embodiments 21-38, wherein the second outer filter layer comprises polyester or polyethersulfone.

Embodiment 40

The bag of any of embodiments 1-39, wherein each of the first and second liquid-permeable tubes comprises a polymer having a total organic carbon (TOC) in water of less than 0.1 mg/cm$^2$.

Embodiment 41

The bag of any of embodiments 1-40, wherein each of the one or more polymer films is gas permeable and comprises a polymer having a total organic carbon (TOC) in water of less than 0.1 mg/cm$^2$.

Embodiment 42

The bag of any of embodiments 1-41, wherein each of the one or more polymer films comprises an elastomer, a fluoropolymer, polymethylpentene (PMP), or any combination thereof.

Embodiment 43

The bag of any of embodiments 1-41, wherein each of the one or more polymer films comprises a fluoropolymer.

Embodiment 44

The bag of embodiment 43, wherein the fluoropolymer is polytetrafluoroethylene (PTFE), perfluoroalkoxyalkane (PFA), ethylene tetrafluoroethylene (ETFE), polyvinylidene fluoride (PVDF), polychlorotrifluoroethylene (PCTFE), ethylene chlorotrifluoroethylene (ECTFE), fluorinated ethylene propylene (FEP), ethylene fluorinated ethylene propylene (EFEP), perfluoropolyether (PFPE), modified polytetrafluoroethylene (TFM), polyvinyl fluoride (PVF), or any mixture thereof.

Embodiment 45

The bag of any of embodiments 1-41, wherein each of the one or more polymer films comprises an inner layer including the fluoropolymer and an outer layer including a silicone elastomer, the inner layer of each film forming the interior compartment of the bag and the outer layer of each film forming the exterior surface of the bag.

Embodiment 46

A bag comprising
one or more polymer films, having edges bonded together to form edges around an undivided interior compartment of the bag;
a first port formed in an exterior surface of the bag;
a first liquid-permeable tube extending into and in fluid communication with the interior compartment of the bag, the first tube being operatively coupled to the first port;
a second port formed in an exterior surface of the bag;
a second liquid-permeable tube extending into and in fluid communication with the interior compartment of the bag, the second tube being operatively coupled to the second port; and
optionally, a third port formed in an exterior surface of the bag, the third port being in fluid communication with the interior compartment of the bag;

wherein the first tube has an average pore size of no more than 50 microns.

Embodiment 47

The bag of embodiment 46, wherein the first tube has a pore size as described for the first outer filter layer in any of embodiments 11-19.

Embodiment 48

The bag of embodiment 46 or embodiment 47, wherein the second tube has an average pore size of no more than 50 microns.

Embodiment 49

The bag of embodiment 48, wherein the second tube has a pore size as described for the second outer filter layer in any of embodiments 30-38.

Embodiment 50

The bag of any of embodiments 46-49, as further described with respect to any of embodiments 2 and 40-45.

Embodiment 51

A cell culture system comprising the bag of any of embodiments 1-50 oriented on a support such that the first and second liquid-permeable tubes are elevated relative to a majority of the first polymer film of the bag.

Embodiment 52

A cell culture system comprising the bag of any of embodiments 1-50 oriented on a support such that the first liquid-permeable tube is elevated relative to the second liquid-permeable tube.

Embodiment 53

A method for cultivating cells, comprising
providing the bag of any of embodiments 1-52 or the system of embodiment 55 or 56 including media and cells in the interior compartment; and
flowing media through the interior compartment by adding media through the second port and through the second liquid-permeable tube and removing media through the first liquid-permeable tube and through the first port.

Embodiment 54

The method of embodiment 53, further comprising removing cultivated cells, e.g., through the third port when one is present.

Embodiment 53

The method of embodiment 53 or embodiment 54 (e.g., wherein a second outer filter layer is included), and wherein the method further comprises, after flowing media through the interior compartment by adding media through the second port and through the second liquid-permeable tube and removing media through the first liquid-permeable tube and through the first port, reversing the direction of flow by flowing media through the interior compartment by adding media through the first port and through the first liquid-permeable tube and removing media through the second liquid-permeable tube and through the second port.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of various embodiments of the of the disclosure in more detail than is necessary for the fundamental understanding of the systems and methods described herein, the description taken with the drawings and/or examples making apparent to those skilled in the art how the several forms of the systems and methods described herein may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the systems and methods described herein (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the systems and methods described herein and does not pose a limitation on the scope of the systems and methods otherwise claimed. No language in the specification should be construed as indicating any non-claimed element essential to the practice of the systems and methods described herein.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless indicated to the contrary, the numerical parameters set forth in the specification and attached claims are approximations that may vary depending upon the desired properties sought to be obtained by the present systems and methods of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the systems and methods of the present disclosure are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the systems and methods disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of systems and methods are described herein, including the best mode known to the inventors for carrying out the systems and methods of the present disclosure. Of course, variations on these described embodiments will become apparent to those of ordinary skill in the art upon reading the foregoing description. The inventor expects skilled artisans to employ such variations as appropriate, and the inventors intend for the systems and methods of the present disclosure to be practiced otherwise than specifically described herein. Accordingly, this disclosure contemplates all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Numerous references have been made to patents and printed publications throughout this specification. Each of the cited references and printed publications are individually incorporated herein by reference in their entirety.

Furthermore, it is to be understood that the embodiments disclosed herein are illustrative of the principles of the present disclosure. Other modifications that may be employed are within the scope of the disclosure. Thus, by way of example, but not of limitation, alternative configurations of the systems and methods of the present disclosure may be utilized in accordance with the teachings herein. Accordingly, the present disclosure is not limited to that precisely as shown and described.

We claim:

1. A bag comprising:
   one or more polymer films, having edges bonded together to form edges around an undivided interior compartment of the bag;
   a first port formed in an exterior surface of the bag;
   a first liquid-permeable tube extending into and in fluid communication with the interior compartment of the bag, the first liquid-permeable tube being operatively coupled to the first port;
   a second port formed in an exterior surface of the bag;
   a second liquid-permeable tube extending into and in fluid communication with the interior compartment of the bag, the second liquid-permeable tube being operatively coupled to the second port; and
   optionally, a third port formed in an exterior surface of the bag, the third port being in fluid communication with the interior compartment of the bag;
   wherein the first liquid-permeable tube comprises:
      a first inner support structure defining a central lumen of the first liquid-permeable tube, wherein the first inner support structure comprises a first porous tube having an average pore size in the range of 250 to 5000 µm; and
      a first outer filter layer surrounding the first inner support structure, wherein the first outer filter layer has an average pore size of less than 50 µm.

2. The bag of claim 1, wherein the one or more polymer films include a first polymer film and a second polymer film, having edges bonded together to form edges around an undivided interior compartment of the bag.

3. The bag of claim 1, wherein the first porous tube has an average pore size in the range of 500 µm to 5,000 µm.

4. The bag of claim 1, wherein the first porous tube has an average pore size in the range of 1000 µm to 5,000 µm.

5. The bag of claim 1, wherein the first porous tube has a porosity in the range of 10% to 90%.

6. The bag of claim 1, wherein at least 60% of the porosity of the first porous tube is localized on a surface opposite the second liquid-permeable tube.

7. The bag of claim 1, wherein the first outer filter layer has an average pore size of less than 20 µm.

8. The bag of claim 1, wherein the first outer filter layer has an average pore size of less than 10 µm.

9. The bag of claim 8, wherein the first outer filter layer has an average pore size of at least 1000 nm.

10. The bag of claim 1, wherein the average pore size of the first outer filter layer is in the range of 5 microns to 50 microns.

11. The bag of claim 1, wherein the second liquid-permeable tube comprises a second inner support structure defining a central lumen of the second liquid-permeable tube and a second outer filter layer surrounding the second inner support structure.

12. The bag of claim 11, wherein the second inner support structure comprises a spiral-wound filament or a second porous tube.

13. A cell culture system comprising the of bag claim 1 oriented on a support such that the first and second liquid-permeable tubes are elevated relative to a majority of the first polymer film of the bag.

14. A cell culture system comprising the bag of claim 1 oriented on a support such that the first liquid-permeable tube is elevated relative to the second liquid-permeable tube.

15. A method for cultivating cells, comprising
   providing the bag of claim 1 including media and cells in the interior compartment; and
   flowing media through the interior compartment by adding media through the second port and through the second liquid-permeable tube and removing media through the first liquid-permeable tube and through the first port.

16. The method of claim 15, further comprising removing cultivated cells from the bag.

17. The method of claim 15, wherein the method further comprises, after flowing media through the interior compartment by adding media through the second port and through the second liquid-permeable tube and removing media through the first liquid-permeable tube and through the first port, reversing the direction of flow by flowing media through the interior compartment by adding media through the first port and through the first liquid-permeable tube and removing media through the second liquid-permeable tube and through the second port.

18. A bag comprising:
   one or more polymer films, having edges bonded together to form edges around an undivided interior compartment of the bag;
   a first port formed in an exterior surface of the bag;
   a first liquid-permeable tube extending into and in fluid communication with the interior compartment of the bag, the first liquid-permeable tube being operatively coupled to the first port;
   a second port formed in an exterior surface of the bag;
   a second liquid-permeable tube extending into and in fluid communication with the interior compartment of the bag, the second liquid-permeable tube being operatively coupled to the second port; and
   optionally, a third port formed in an exterior surface of the bag, the third port being in fluid communication with the interior compartment of the bag;
   wherein the first liquid-permeable tube comprises
      a first inner support structure defining a central lumen of the first liquid-permeable tube, wherein the first inner support structure comprises a spiral-wound filament, wherein a spacing of the spiral-wound filament is at least 100 µm; and
      a first outer filter layer surrounding the first inner support structure, wherein the first outer filter layer has an average pore size of less than 50 µm.

19. The bag of claim 18, wherein the spacing of the spiral-wound filament is in the range of 100 µm to 10 mm.

20. The bag of claim 18, wherein the spacing of the spiral-wound filament is in the range of 500 µm to 7.5 mm.

* * * * *